US00PP08732P

United States Patent [19]

van Andel

[11] Patent Number: Plant 8,732

[45] Date of Patent: May 17, 1994

[54] CARNATION NAMED STAGIWIT

[75] Inventor: Jacob van Andel, Aalsmeer, Netherlands

[73] Assignee: Van Staaveren B.V., Aalsmeer, Netherlands

[21] Appl. No.: 21,843

[22] Filed: Feb. 24, 1993

[51] Int. Cl.[5] ..... A01H 5/00

[52] U.S. Cl. ..... Plt./70.3

[58] Field of Search ..... Plt. 70.2, 70.3

*Primary Examiner*—James R. Feyrer
*Assistant Examiner*—Erich E. Veitenheimer
*Attorney, Agent, or Firm*—Tilton, Fallon, Lungmus & Chestnut

[57] ABSTRACT

A new and distinctive spray carnation cultivar particularly distinguished by its profuse, intermittent production of small sized white flowers borne in a cluster of five petals on strong, upright stems.

1 Drawing Sheet

BACKGROUND OF THE NEW PLANT

This carnation cultivar originated as a hybrid seedling produced in my nursery at Aalsmeer, Holland, by my crossing of two plants, hereinafter identified, selected from a field of various carnation varieties maintained at my nursery for breeding purposes. This particular seedling was selected from those produced by the said hybridization because of the unusual petal shape and uniform coloraton and its sturdy, fast growing growth habit. This hybrid most closely resembles Statropur. This selected seedling was propagated by me at Aalsmeer, Holland, by cuttings with very satisfactory results and thereafter this selected plant was propagated through several successive generations in the same manner which demonstrated conclusively that the novel characteristics of the originally selected seedling would be maintained from generation to generation and its homogeneity would be firmly established.

DESCRIPTION OF THE DRAWING

My new spray carnation plant is illustrated by the accompanying photographic drawing which, in full color, shows the form and coloration of the flowers as they appear with relatively close spacing at the upper end portion of the flowering stem of the plant. The colors shown are as nearly true to these herein specified as is reasonably possible to obtain by conventional photographic procedures.

DESCRIPTION OF THE NEW PLANT

The following is a detailed description of my new carnation plant as observed from plants grown under greenhouse conditions in Aalsmeer, Holland, with the stated flower colors being according to the R.H.S. Colour Chart of The Royal Horticultural Society of London, England.

THE PLANT

Origin: Seedling.

Parentage:

*Seed parent.*—8921-1Z (unpatented).

*Pollen parent.*—8070-S (unpatented).

These parent plants are so identified in my business records of the present cultivar maintained at the offices of the Aalsmeer, Holland, nursery and the production of the aforementioned hybrid and the selected seedling are also there recorded.

Classification:

*Botanic.*—*Dianthus caryophyllus.* The parent plants are proprietary.

*Commercial.*—Spray carnation.

Form: An upright bush.

Height: 100 cm.

Growth rate: Fast.

Main stem length: About 80–90 cm.

Strength: Strong.

Branching character: The main stem has 2–4 sidebranches and each sidebranch has 1–2 sidebranches.

Growth: Upright.

Foliage:

*Quantity.*—Medium.

*Number of leaves.*—16–20.

*Size and shape of leaf.*—The leaf is lanceolet shaped, and about 8–12 cm in length and 1–2 cm in width.

*Margin type.*—Straight.

*Texture.*—Smooth.

*Color.*—Upper side — RHS 137A. Under side — RHS 137C.

THE BUD

Size:

*Shape.*—Cylindrical.

*Diameter.*—3 mm.

*Length.*—20 mm.

Color of petals:

*When sepals first divide.*—White (RHS 155D). When petals begin to unfurl. White (RHS 155D).

Calyx:

*Shape.*—Cylindrical. The calyx is formed out of five points fused sepals, which are joined together at the lower part.

*Aspect.*—Smooth.

*Size.*—3 mm wide and 20 mm long.

*Color.*—RHS 139C.

THE FLOWER

Blooming habit: Intermittent and profuse — Early Spring and Fall.

Size of bloom: Small.

*Diameter.*—3.0 cm.

*Depth.*—0.5 cm. The depth of the bloom is measured from the top of the calyx to the point where the petals group around the pistil.

Borne: In a cluster in a tight panicle.

Shape: When bloom first opens it is flat. When bloom matures it is funnel shaped. In addition, a deep corolla is formed by the petal bases.

*Uniformity of blossoms.*—The secondary blossoms are the same size as the primary blossoms, however, later in the season when there is less light, the secondary blossoms are a little smaller.

*Frequency of flower opening.*—The secondary flowers open synchronously with the primary flowers.

Petalage:

*Number of petals.*—Five.

*Arrangement.*—Side by side round pistil.

*Texture.*—Soft.

*Form.*—Fanshaped.

*Apex.*—Deep incissions.

*Margin type.*—Dentate at the apex.

*Appearance.*—Satiny.

*Color.*—Outer petal: White (RHS 155D). Body: White (RHS 155D). Base: White (RHS 155D). Reverse side: White (RHS 155D).

Remain on stem: Petals stay on the stem for 3 weeks.

Discoloration after full bloom: Turns a little creamy color.

Persistence: The petals of matured flowers hang on and dry.

Fragrance: Strong.

Lasting quality:

*On the plant.*—About 3 weeks.

*As cut flower.*—About 12 days.

Disease resistance: *Fusarium oxysporum.*

Flower stem:

*Length.*—About 1 cm.

*Character.*—Upright and strong. Color.—RHS 137C.

THE REPRODUCTIVE ORGANS

Stamens:

*Number.*—About 10.

*Arrangement.*—Side by side in a circule around the pistil.

*Anthers.*—Size: 2 mm. Color: Pink (RHS 77B).

*Filaments.*—Length: 2 cm. Color: White (RHS 155D).

*Pollen.*—Color: White (RHS 155D).

Pistils:

*Number.*—One.

Styles: Length about 0.5 to 1.0 cm

*Color.*—White (RHS (155D).

*Stigmas.*—White (RHS 155D).

Characteristics of ovaries:

*Fertile.*—No.

*Shape.*—Pear-shaped.

I claim:

1. A new and distinctive spray carnation plant, substantially as herein shown and described.

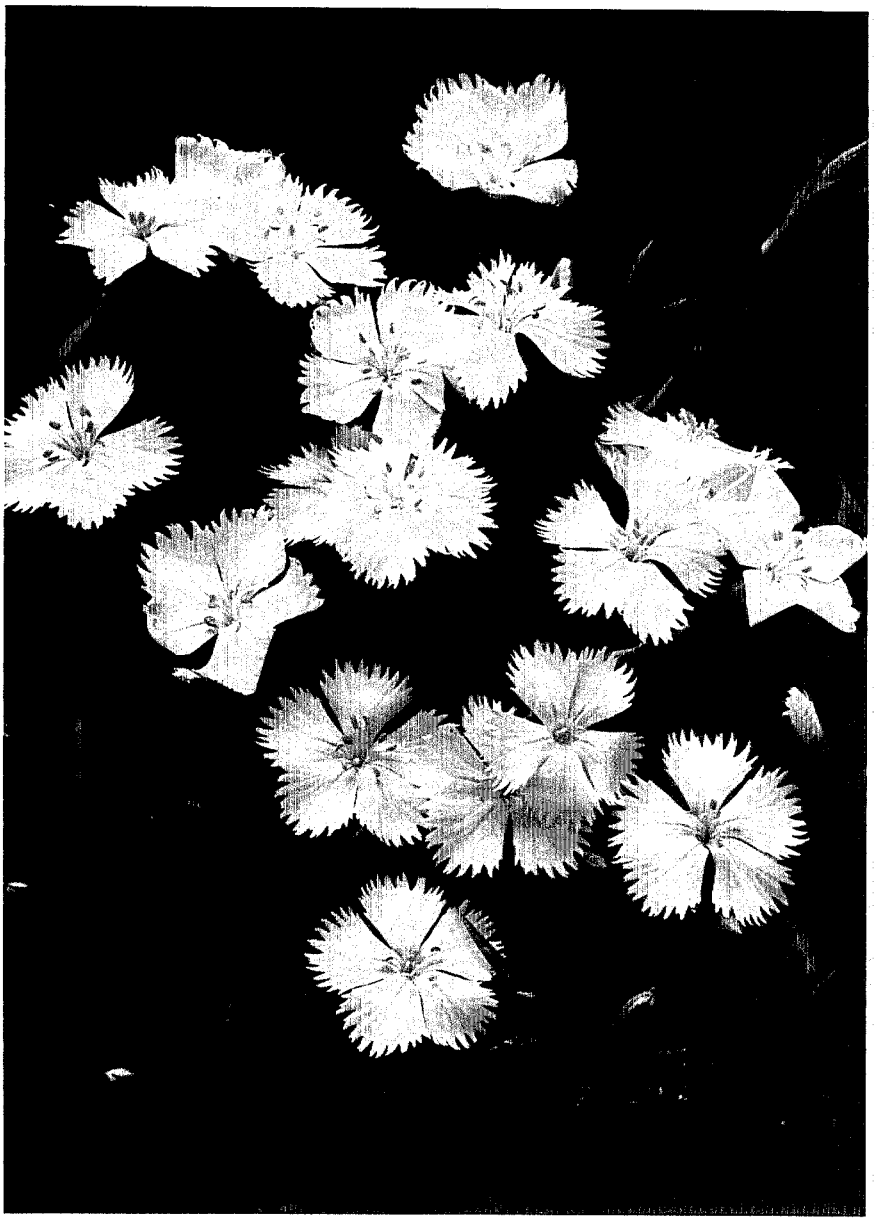

* * * * *